United States Patent [19]

Moerke

[11] Patent Number: 5,597,385
[45] Date of Patent: Jan. 28, 1997

[54] FILTERED EXHAUST WAND FOR REMOVING LASER SMOKE

[75] Inventor: Duane C. Moerke, Bloomington, Minn.

[73] Assignee: Moerke Custom Products, Inc., Bloomington, Minn.

[21] Appl. No.: 343,336

[22] Filed: Nov. 21, 1994

[51] Int. Cl.$^6$ .................................................. B01D 39/00
[52] U.S. Cl. ................................ 55/274; 55/357; 55/383; 55/473; 55/505
[58] Field of Search ......................... 55/274, 383, 385.1, 55/467, 473, 503, 505, DIG. 18; 604/49, 902

[56] References Cited

U.S. PATENT DOCUMENTS

| | | |
|---|---|---|
| 3,464,556 | 9/1969 | Cullen . |
| 4,468,217 | 8/1984 | Kuzmick et al. ........................ 604/48 |
| 4,619,672 | 10/1986 | Robertson ................................ 55/316 |
| 4,790,811 | 12/1988 | Bloxom, Jr. . |
| 4,796,795 | 1/1989 | Urban ...................................... 228/20 |
| 4,819,577 | 4/1989 | Campau . |
| 4,886,492 | 12/1989 | Brooke . |
| 4,921,492 | 5/1990 | Schultz et al. . |
| 5,047,072 | 9/1991 | Wertz et al. . |
| 5,156,618 | 10/1992 | Fiore et al. . |
| 5,181,916 | 1/1993 | Reynolds et al. . |
| 5,211,639 | 5/1993 | Wilk . |
| 5,264,026 | 11/1993 | Paul . |
| 5,275,596 | 1/1994 | Long et al. . |
| 5,281,246 | 1/1994 | Ray et al. .............................. 55/302 |
| 5,312,465 | 5/1994 | Riutta .................................... 55/320 |
| 5,409,511 | 4/1995 | Paul ...................................... 55/218 |

OTHER PUBLICATIONS

Article by Kay A. Ball entitled "Controlling Smoke Evacuation and Odor During Laser Surgery", *Today's OR Nurse*, vol. 8, No. 12 (Dec. 1986), pp. 4–10.

Article entitled "Smoke evacuator for laser surgery" by Gale W. Miller, M.D., et al, Drug/Device Capsule (Oct. 1983), pp. 582–583.

Article entitled "Medical Gas Systems:Balancing Cost and New Technology" by Jerry L. Van Norman, Plumbing Engineer (Jul./Aug. 1994).

Brochure, Ohmeda, "Ohio OR Systems Delivery Support Services Safely" (copyright 1982).

Brochure, Ohio Medical Products "Modular Rigid Surgery Ceiling Column" (May 1, 1985).

Brochure, 3M, "3M Filtrete Air Filter Media: Catch Particles With Near–Perfect Efficiency" (copyright 1993).

Brochure, 3M, "It's Not Just An Air Filter, It's An Obstacle Course" (copyright 1992).

*Primary Examiner*—David W. Wu
*Attorney, Agent, or Firm*—Frederick W. Niebuhr, Esq.; Haugen and Nikolai, P.A.

[57] ABSTRACT

An exhaust system, including a hand-held exhaust wand is employed to remove laser smoke plumes generated at a surgical site. The wand includes a transparent cylindrical shroud containing a conical filter that diverges in the proximal direction. An adapter, removably coupled to the shroud at its proximal end, enables coupling of the wand to standard vacuum tubing, connectors and other components for exhausting air that flows through the wand. The wand is positioned with its distal end confronting the surgical site, whereby plumes and odor generated at the site are immediately drawn into the wand through its distal opening. As air passes through the filter toward a proximal opening of the wand, the conical filter traps the airborne contaminants to protect against contamination of downstream components. The removable coupling of the shroud enables convenient exchange of the filter. For surgeries that present a higher risk of contamination, the entire wand can be discarded to effect a safe disposal of trapped contaminants.

14 Claims, 3 Drawing Sheets

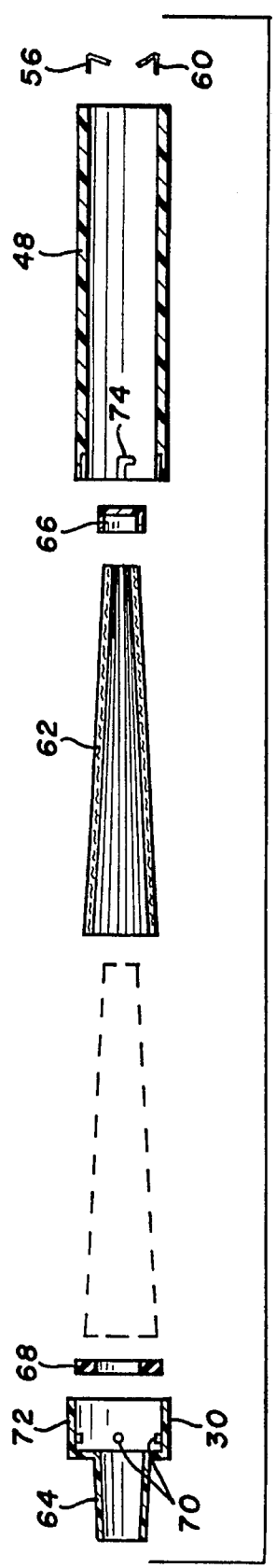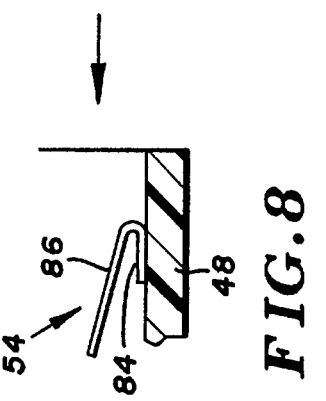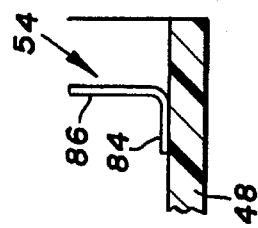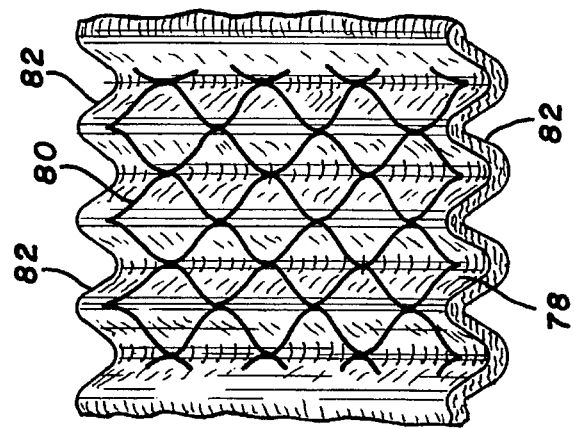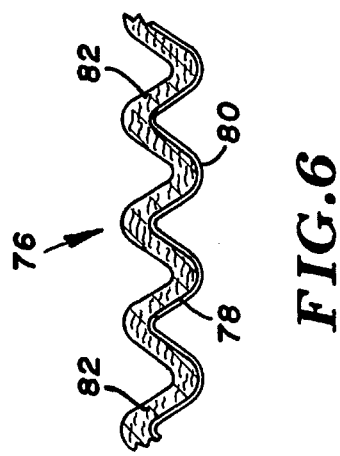

FILTERED EXHAUST WAND FOR REMOVING LASER SMOKE

BACKGROUND OF THE INVENTION

The present invention relates to apparatus for protecting the patient and medical personnel during a surgical procedure, and more particularly to devices and systems for the removal and disposal of smoke particles, vaporized tissue and other airborne debris and contaminants that arise during laser surgery and other surgeries.

The use of lasers in surgical procedures has gained wide acceptance, due to the high degree of accuracy with which laser energy can be applied to form incisions, cauterize incised vessels and otherwise treat tissue. While particularly well suited to eye surgery and other microsurgery, lasers have gained acceptance in areas well beyond microsurgery.

Widespread use has given rise to increased efforts to counteract a significant problem of laser surgery, namely the laser smoke or plume emitted at the surgical site during surgery. The laser-generated plume is known to contain hydrocarbons, carbon monoxide and moisture. Laser smoke typically has an extremely unpleasant odor, and is sufficiently dense to interfere with the physician's view of the surgical site. At least one virus, Human Papillomavirus DNA, is known to survive a laser surgery procedure and may pose a health risk if it occupies the operating room environment. The HIV virus that can lead to AIDS also is a source of concern, although it is not yet known with certainty whether the HIV virus can survive a laser surgery procedure.

Operating rooms require a positive pressure in relation to adjacent spaces. This tends to maintain sterility within the operating room, by preventing airborne contaminants from entering the room. A further result of the positive pressure, however, is that contaminants and odors are likely to permeate the operating room and contaminate adjacent areas, if not captured at the surgical site.

Systems and apparatus have been developed in an effort to solve this problem. For example, U.S. Pat. No. 5,264,026 (Paul) discloses a laser plume evacuation system with articulating arms that support disposal flexible tubing near the operating table. The articulating arms conduct exhaust from the tubing to a main located above the operating room ceiling. From the main, air is conducted to a centrifugal separator tank and then to a fan that produces the vacuum. Downstream of the fan is a high efficiency particle air (HEPA) filter. This system is expensive and requires considerable maintenance to reduce contamination throughout the system.

An alternative, more portable approach, is a laser smoke filtration system offered by Stackhouse Incorporated of El Segundo, Calif. This system, contained for the most part in a housing mounted on wheels, includes disposable vacuum tubing, a disposable canister filter for odor adsorption, internal filters and a means for returning diffused, filtered air to the operating room. However, the vacuum hose and pick-up shroud, much like the various upstream elements in the above-discussed exhaust system, are subject to contamination. Charcoal filters must be maintained or odors will be present in the exhaust returned to the operating room. The unit is expensive, although not so costly as the plume evacuation system described above.

Several patents describe hand-held laser surgery devices that incorporate a vacuum feature for laser smoke removal, e.g. U.S. Pat. No. 5,181,916 (Reynolds et al) and U.S. Pat. No. 5,275,596 (Long et al). These patents contemplate reliance on a central vacuum system for filtering, as they do not feature any filtration means within the devices themselves. Further, these devices inherently involve drawing of the smoke plume directly toward the laser source, unduly interfering with the operator's view of the surgical site during the laser procedure.

Therefore, it is an object of the present invention to provide a means for more safely and effectively removing the airborne product of a laser surgery, clear of the laser device to minimize interference along the line of sight of the physician or other operator.

Another object of the invention is to provide a vacuum system for drawing away the airborne product of laser surgery or other surgeries, in a manner that reduces or eliminates contamination of system components downstream of the wand or other intake housing at the surgical site.

A further object is to provide a wand or other intake housing usable at a laser surgery site, that incorporates a filtration feature and is adapted for coupling to a standard central vacuum, exhaust or other evacuation system.

Yet another object is to provide a low cost and reliable means for disposing of the smoke plume and the offensive odor generated during a laser surgery procedure.

SUMMARY OF THE INVENTION

To achieve these and other objects, there is provided a device for removing the airborne product of a surgical procedure. The device includes an elongate housing having a proximal opening at its proximal end and a distal opening at its distal end. The housing has an internal passageway for accommodating the flow of air from the distal opening to the proximal opening. A partition means, disposed inside of the housing, divides the internal passageway into an upstream chamber in direct fluid communication with the distal opening, and a downstream chamber in direct fluid communication with the proximal opening. The partition means includes a filtering means for allowing the flow of air therethrough. At the same time, the filtering means collects airborne elements within the air flow, thus to prevent the passage of the airborne elements from the upstream chamber to the downstream chamber. Substantially fluid tight means are provided for mounting the partition means to the housing. A vacuum means, downstream of the housing and in fluid communication with the proximal opening, draws air out of the housing through the proximal opening. This in turn draws the flow of air into the housing through the distal opening and through the filtering means into the downstream chamber. The housing is positionable by hand at a location near a surgical site with the distal opening in confronting relation to the surgical site. Thus, the flow of air includes airborne elements generated as a product of a surgical procedure at the surgical site.

The preferred housing is a tubular wand with a substantially cylindrical internal passageway. The filtering means is advantageously a conical filter that diverges in the proximal direction. This increases the available area for filtration of the air flow. The filtering material can be self-supporting, or a conical screen can be provided adjacent the filter for support.

One or more flow indicator strips can be mounted along the internal passageway, preferably near the distal opening. These strips, which bend elastically in response to a proximal flow of air through the passageway, provide a convenient means for visually indicating (at least approximately) the amount of air flowing through the passageway. Any substantial blockage of the filter results in an airflow reduction and the corresponding visual indication by the strips. A transparent housing increases the utility of this feature.

The device can be part of an exhaust system for removing the airborne product and odor of a surgical procedure from an operating room. More particularly, the above-described device is coupled at its proximal end to a section of vacuum tubing. At its opposite end, the tubing is connected with a vacuum or exhaust source. The vacuum source is used to generate the required airflow through the passageway of the wand. An adapter can be provided for coupling the distal end of the vacuum tubing with the proximal end of the wand. The adapter has a proximal portion suited for a frictional engagement with the vacuum tubing. Coupling means at the adapter distal end form a releasable interlock with a complementary coupling means at the proximal end of the wand. The adapter facilitates quick and convenient coupling and decoupling of the wand. Consequently, the wand is easily removed for inspection, replacement of the filter, or for replacement of the wand and filter.

The device and system enable a process for removing the airborne product of a laser surgical procedure from a surgical site, according to the following steps:

a. positioning an elongate tubular wand near a surgical site during a laser surgical procedure, with a distal opening of the tubular wand confronting the surgical site;

b. throughout the surgical procedure, at least during times when airborne product is generated, drawing a vacuum at the proximal end of the tubular wand to generate a flow of air through an internal passageway within the wand; and c. collecting airborne elements including the product of the surgical procedure within the wand, while allowing the flow of air through the internal passageway, whereby air leaving the wand through the proximal opening is substantially free of the airborne product and the airborne product accumulates within the wand.

Thus in accordance with the present invention, the airborne product of a laser or other surgical procedure is immediately and effectively removed from the site of surgery. The wand or other housing is sufficiently small and lightweight to be easily maneuvered by hand, facilitating adjustments to maintain an optimal position throughout surgery. The vacuum or exhaust system downstream of the wand handles air after the filtering stage, and thus is protected from contamination due to the surgical product. The strips mounted in the passageway visually indicate an accumulation of material at the filter that interferes with the free flow of air. At this point, the wand is conveniently removable for replacement of the filter. Alternatively the entire wand can be disposed of and replaced to effect disposal of captured contaminants without the need to hold or touch the filter or the interior of the wand.

THE BRIEF DESCRIPTION OF THE DRAWINGS

For a further understanding of the above and other features and advantages, reference is made to the detailed description and to the drawings, in which:

FIG. 5 is an exploded parts view of the exhaust wand and the adapter;

FIG. 6 is an enlarged end view showing particulate filtration material used in a filter inside the exhaust wand;

FIG. 7 is an plan view of the filtration material, showing a surface that is downstream when the material is employed within the hand-held exhaust wand;

FIGS. 8 and 9 depict an indicator strip mounted along a passageway through the exhaust wand, respectively illustrating satisfactory and unsatisfactory air flow through the wand;

DETAILED DESCRIPTION OF THE PREFERRED EMBODIMENTS

Figure 1:
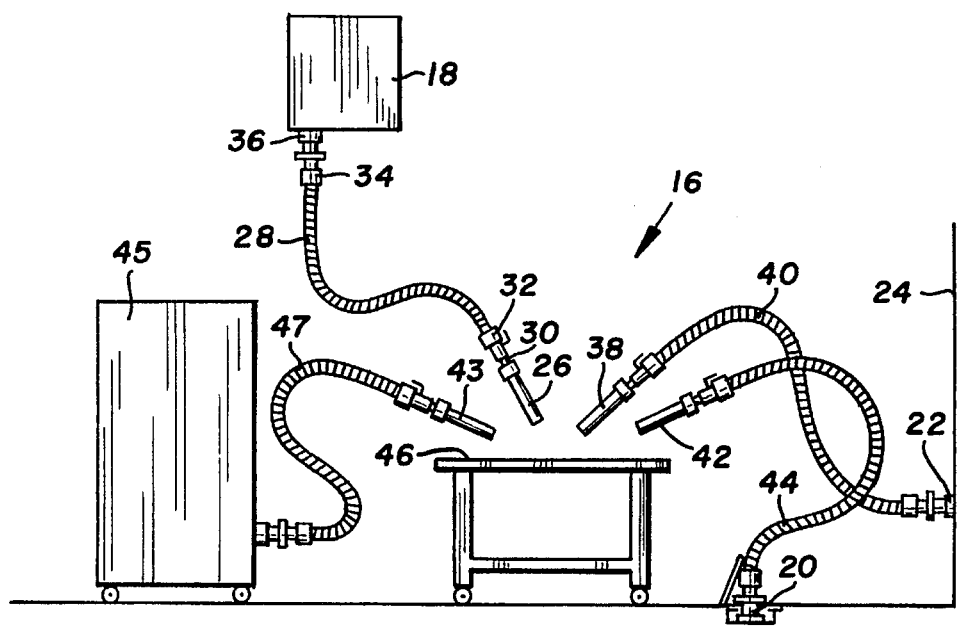
FIG. 1 is a schematic view of an operating room exhaust system constructed in accordance with the present invention and including several alternative exhaust routes.

Turning now to the drawings, FIG. 1 illustrates an exhaust system 16 for removing the airborne product a surgical procedure from a hospital operating room. System 16 incorporates components that provide three alternative routes for exhaust air: upwardly to a medical gas column 18; downwardly to a coupling 20 mounted in the floor of the operating room; and to a coupling 22 mounted in a wall 24 of the operating room. It is to be understood that the four alternatives are shown in one figure as a matter of illustrative convenience. A typical exhaust system requires only one of these alternatives, with the choice depending on the operating room layout and available equipment. Further, although less preferred, the exhaust can be routed to a self-contained recirculation unit within the operating room.

Each route incorporates, at its distal end, a hand-held exhaust wand. For example, a wand 26 is coupled to a section of vacuum tubing 28 through an adapter 30 and a distal end connector 32. At the proximal end of the vacuum tubing is a proximal end connector 34, which is joined to a coupling 36 mounted to medical gas column 18.

In the same manner, an exhaust wand 38 is joined to coupling 22 through a section of vacuum tubing 40, and a wand 42 is Joined to floor mounted coupling 20 through a section of vacuum tubing 44. Yet another exhaust wand 43 is coupled to a portable vacuum system 45 through vacuum tubing 47.

Each of wands 26, 38, 42 and 43 is lightweight and sized for convenient lifting by hand. For example, a cylindrical wand about 10 inches long and about 2 inches in diameter has been found satisfactory. Due to the flexibility and pliability of tubing sections 28, 40, and 44, the exhaust wands are easily maneuverable by hand, both as to their position and orientation. Each of the tubing sections is of sufficient length to enable positioning of the associated wand as desired with respect to an operating table 46, as it is desirable to position the wand as near to the surgical site as possible, without interfering with the procedure.

Figure 2:
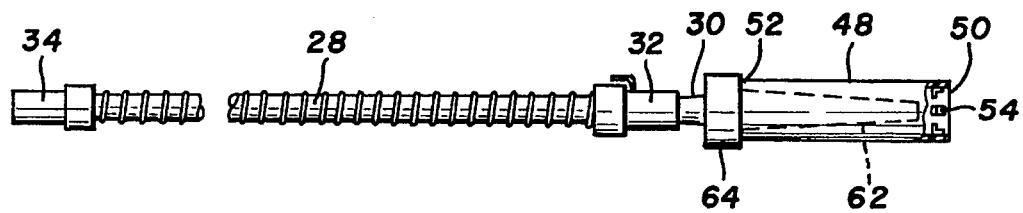
FIG. 2 is a side elevation of several components of the system in FIG. 1, including a hand-held exhaust wand, an adapter, a vacuum hose and a connection to a hospital vacuum source.

FIG. 2 illustrates wand 26 and its associated components in greater detail. The wand includes a cylindrical shroud 48 preferably constructed of a transparent plastic. The shroud thus forms a cylindrical air flow passageway from a distal end opening 50 to a proximal end opening 52 of the shroud. Several air flow indicator strips 54, 56, 58 and 60 are mounted along the internal passageway near the distal end. Shroud 48 contains a conical filter 62, which is discussed below in connection with FIGS. 5–7. Conical filter 62 provides a partition means, dividing the inner passageway into an upstream chamber in fluid communication with distal end opening 50 and downstream chamber in direct fluid communication with proximal end opening 52.

Adapter 30 is coupled to the proximal end of the shroud and incorporates means at its distal end to achieve an interlocking engagement. A proximal section 64 of the adapter has an outer diameter of 1¼ inches to facilitate a slip fit, i.e. frictional coupling, with standard vacuum hose sections.

Figure 3:
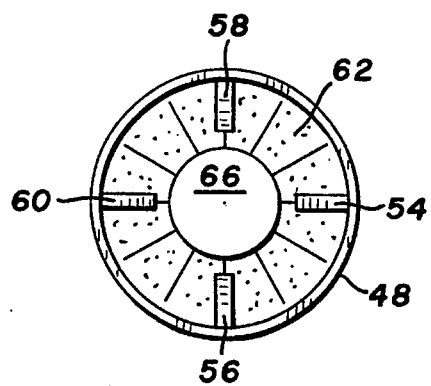
FIG. 3 is a distal end view of the exhaust wand.

The distal end view of the wand in FIG. 3 illustrates the air flow indicator strips. Also visible in this figure is the upstream surface conical filter 62 and an end cap 66 at the distal end of the filter.

Figure 4:
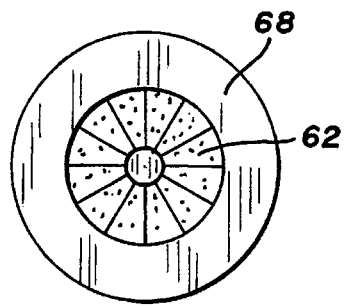
FIG. 4 is a proximal end view of the exhaust wand.

FIG. 4 is a proximal end view of wand 26, removed from adapter 30. Visible in this view is an annular base seal 68, preferably a washer formed of rubber, which is sealed to the proximal end of conical filter 62. Base seal 68 is elastically deformed when adapter 30 and exhaust wand 26 are coupled, to form a fluid tight seal. Similarly, end cap 66 is sealed to the proximal end of conical filter 62 in fluid-tight fashion. Thus, to reach the proximal end of the wand, air from distal opening 50 must travel through filter 62.

As seen in FIG. 5, a plurality of pins 70 are mounted to a distal section 72 of adapter 30, each pin extending radially inward. A corresponding set of locking slots 74 are formed in shroud 48. Each of the locking slots is open to the proximal end and to the internal passageway. Each slot includes an axial segment and, at its distal end, a segment perpendicular to the axial segment. All perpendicular segments of the locking slots extend in the same direction. Accordingly, adapter 30 and shroud 48 are interlocked by moving them together axially after the pins and slots are properly aligned, and then by rotating these components relative to one another. At this stage, base seal 68 is resiliently compressed and assists in maintaining the interlocking engagement due to its elastic restoring force. Thus, pins 70 and slots 74 provide complementary coupling means in adapter 30 and shroud 48, respectively.

FIGS. 6 and 7 illustrate one preferred filtration medium used to form conical filter 62. One such preferred filtration medium is available from 3M Company of St. Paul, Minn., under the brand name 3M Filtrete. The filters are available in a variety of weights ranging from 30–300 grams (per square meter), weights of 85 grams and below are preferred. In FIG. 6, a section 76 of the medium is shown in end view, to reveal a pleated construction. On a downstream side 78, the medium incorporates a wire mesh or screen 80, which structurally supports the medium and defines the pleats shown at 82. Screen 80 has generally diamond shaped openings and creates a series of elongate, parallel pleats in the filter material.

Screen 80 is sufficiently malleable to permit a shaping of the medium into the desired conical form with the elongate pleats extending substantially in the axial direction, except for the radially inward incline required for a distal convergence of the cone. The conical shape of filter 62, and the pleats formed in the filtering medium, cooperate to substantially increase the surface of the filter (for example as compared to a disk shaped filter normal to shroud extension). Accordingly, the filtration capacity of the wand is considerably improved and the time between required filter exchanges is considerably increased. Filtration media that does not incorporate a screen (or otherwise is not self-supported) may also be employed if used with a conical mesh framework adjacent and immediately downstream of the medium to provide the necessary structural support.

FIGS. 8 and 9 illustrate the function of air flow indicator strip 54. The strip is located along the internal passageway near distal end of the shroud. A mounting segment 84 of the strip is secured to the shroud, e.g. by a suitable adhesive, leaving a free end segment 86 of the strip as the majority of the strip length.

Strip 54 is constructed of an elastically deformable material, e.g. nylon netting. In FIG. 8, an air flow (indicated by the arrow) causes strip free end segment 86 to pivot such that the free end points generally in the proximal direction. By contrast, in the absence of sufficient air flow, the free end of the strip tends to extend approximately radially (i.e. vertically in FIG. 9). This would be the normal, unstressed configuration for the strip when exhaust wand 26 is not in use. However, during usage the configuration of FIG. 9 indicates lack of a sufficient flow of air through the internal passageway, perhaps due to a partial or complete blockage of conical filter 62. Indicator strips 56, 58 and 60 function in the same manner as strip 54.

During a surgical procedure the wand operator observes the configurations of the indicator strips. Should the strips begin to revert to a radial, rather than proximal extension of the free ends, the operator is alerted to the need to replace filter 62, replace the entire wand, or address a possible system malfunction.

Figure 10:
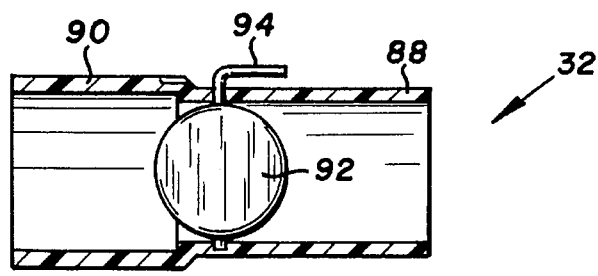
FIG. 10 is a side elevation, in section, of a vacuum tubing distal end connector incorporating a damper.

FIG. 10 illustrates vacuum tubing distal end connector 32 in greater detail. A distal end section 88 of the connector is adapted for the aforementioned slip fit with proximal section 64 of adapter 30. A proximal end section 90 of the connector is coupled to vacuum tubing section 28.

Mounted within connector 32 to pivot on a transverse axis (vertical in FIG. 10) is a disk shaped damper blade 92. A damper lever 94 outside of the connector is operable to selectively position the damper blade between an open position as shown and a closed position in which the blade is perpendicular to the direction of air flow. Through lever 94, the damper blade can be manipulated to control the rate of air passage through the connector, and thus control the rate of air flow through the internal passageway of the exhaust wand. Damper blade 92 thus is operable as a valve to regulate the air flow.

Figure 11:
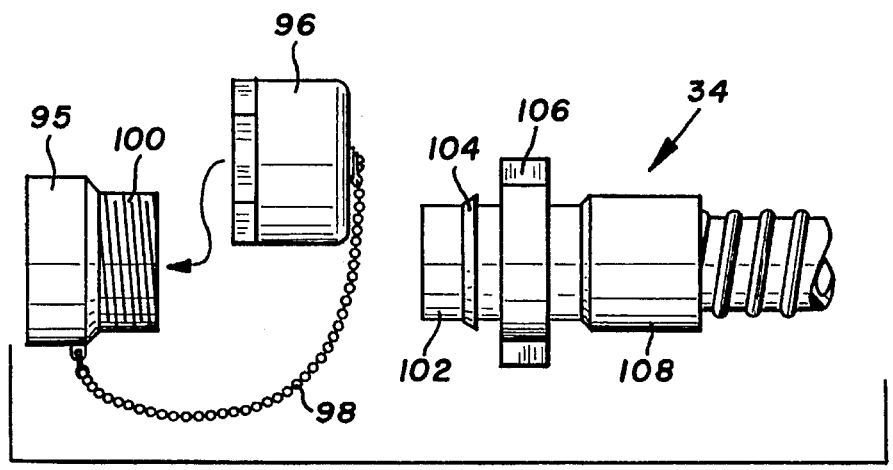
FIG. 11 is a side elevation showing a vacuum hose proximal end connector and a coupling to a hospital vacuum system.

FIG. 11 illustrates vacuum tube section proximal connector 34 and a coupling 95 of a hospital vacuum or exhaust system, e.g. such as wall mounted coupling 22 in FIG. 1. The coupling is permanently mounted and can include a cap 96 secured by a chain 98, and having internal threads corresponding to external threads 100 of the coupler. When the coupler is not in use, the cap is threadedly engaged to reduce contamination.

Proximal connector 34 has a proximal end section 102 designed to fit slidably into coupling 94 until a friction-fit retaining ring 104 abuts the coupler. At this point, an internally threaded fastener 106 is threaded onto external threads 100, which secures the proximal connector. A distal portion section 108 of the connector is attached to the proximal end of vacuum tubing section 28, either permanently or in frictional slip-fit fashion.

When used during a laser surgical procedure, exhaust wand 26 is coupled to tubing section 28 through adapter 30 and distal connector 32. The tubing in turn is connected to the coupler of a hospital-vacuum or exhaust system through proximal connector 34. With these connections complete, the vacuum power source of the hospital system continually draws air into the internal passageway through distal opening 50 and into the upstream chamber of the passageway, through filter 62 to the downstream chamber, out of the wand through the proximal end and proximally through tubing section 28, ultimately to the vacuum source. During surgery, as the laser beam encounters tissue, a plume of laser smoke is generated at the surgical site. The plume causes an offensive odor and includes airborne elements such as particulates and aerosols, some of which are potentially harmful to the patient and personnel in the operating room. Collectively, the airborne elements scatter and absorb light near the point of surgery. This interferes with a clear visual perception of the site, causing delay or increasing the risk of patient injury. If the plume is not removed, an objectionable odor permeates the operating room.

Accordingly, a rapid removal of the laser smoke plume enhances surgery, particularly if accomplished at minimal interference with the procedure. These goals are achieved according to the present invention in that exhaust wand 26 is held and maneuvered easily by hand, entirely independently of the surgical laser device. Thus, the operator is free to position the exhaust wand at any desired location and orientation with respect to the surgical laser. The exhaust wand is preferably positioned with its distal extension toward the surgical site, with distal end 50 confronting the surgical site. This effects a rapid and substantially complete removal of each plume of laser smoke as it is generated.

Thus, particulates and other airborne elements become part of an air flow through the exhaust wand. As the air flow moves through conical filter, the airborne elements are removed (of course, within the efficiency limits of the filter). Downstream of the filter, the air flow is substantially free of the airborne contamination, thus to protect the downstream components including the vacuum tubing and reduce the contamination entering the hospital vacuum or exhaust system.

If, during the surgical procedure, the air flow indicator strips show a reduction in air flow through the wand, the surgical procedure is momentarily interrupted to enable an exchange of the filter, or of the entire wand. Replacing the entire wand is recommended particularly where the presence of harmful airborne contamination is suspected. The interchange of wands is quick and convenient due to the interlocking engagement. Disposal of the wand can be accomplished without any contact with airborne elements captured by the filter.

The need for such exchanges of course depends upon the nature of the surgery, but is minimized due to the conical shape and pleating of the filtration media, both of which substantially increase the available surface area for filtration. At the same time, at least the filter should be exchanged with every surgical procedure.

Figure 12:
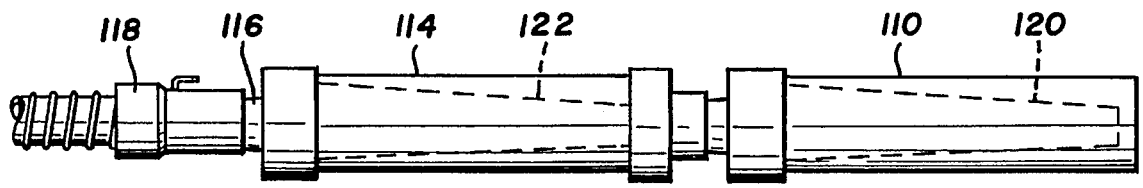
FIG. 12 schematically illustrates an alternative embodiment device incorporating two filtration stages.

FIG. 12 illustrates, in part, an alternative embodiment laser plume exhaust system employing two exhaust wands in series, thereby to provide two filtration stages. More particularly, the system includes a distal wand 110, an adapter 112 coupled to the proximal end of the distal wand, a proximal wand 114 coupled to adapter 112, an adapter 116 at the proximal end of the proximal wand, and a connector 118 at the distal end of a vacuum tubing section (not shown). Each of the wands incorporates a conical filter, as indicated in broken lines at 120 and 122, respectively. In addition to an increased filtration capacity and further reduction of contamination downstream, the two-stage approach affords the opportunity to selectively size filters 120 and 122. For example, upstream filter 120 can be sized to filter contaminants of greater than a selected size, e.g. 5 microns. The downstream filter 122 can be sized to filter finer particles, e.g. down to a submicron limit.

Thus in accordance with the present invention, plumes of potentially hazardous smoke, and their objectionable odors, generated during laser surgery are removed from the surgical site and surrounding area. Removal can be immediate and substantially complete, since the hand-held wand is easily positionable with its distal end confronting the surgical site. Filtration occurs in the wand itself, substantially eliminating contamination of system components downstream of the exhaust wand. This reduces the need to clean these downstream components, reduces the cost of maintaining them, and extends their useful life. Exhaust wand filtration also reduces the risk to maintenance personnel, by reducing their exposure to hazardous contaminants when cleaning, repairing or adding components to the central vacuum or exhaust system. The arrangement further facilitates a safe disposal of filtered airborne contaminants, since the entire wand can be discarded without any direct contact with contaminants trapped in the filter. The exhaust wand is easily retrofit to standard vacuum system components, and eliminates the need for complex and expensive filtration schemes in the central vacuum or exhaust system, because of the wand's upstream filtration capabilities.

What is claimed is:

1. A device for removing the airborne elements generated as a product of a surgical procedure; including:

an elongate housing having a proximal opening at its proximal end and a distal opening at its distal end, and defining an internal passageway for accommodating a flow of air from the distal opening to the proximal opening;

a partition means disposed inside of the housing for dividing the internal passageway into an upstream chamber in direct fluid communication with the distal opening, and a downstream chamber in direct fluid communication with the proximal opening; said partition means including a filtering means for allowing the flow of air therethrough while collecting airborne elements within the air flow, thus to prevent passage of the airborne elements from the upstream chamber to the downstream chamber;

a means for mounting the partition means to the housing; and a vacuum means, downstream of the housing and in fluid communication with the proximal opening, for drawing air out of the housing through the proximal opening, thus to generate the flow of air into the housing through the distal opening and through the filtering means into the downstream chamber;

wherein the housing is positionable by hand at a location near a surgical site with the distal opening in confronting relation to the surgical site, whereby said flow of air as it enters the housing includes airborne elements generated as a product of a surgical procedure at the surgical site.

2. The device of claim 1 wherein:

an housing comprises a tubular wand that defines the internal passageway.

3. The device of claim 2 wherein:

the filtering means comprises a conical filter that diverges in the proximal direction.

4. The device of claim 3 wherein:

the partition means includes a conical screen adjacent the filter and supporting the filter.

5. The device of claim 1 further including:

indicating means, mounted to the housing, for indicating the flow of air through the internal passageway.

6. The device of claim 5 wherein:

said housing is transparent, and the indicating means comprise at least one indicator strip mounted with respect to the housing in the internal passageway proximate the distal opening, the indicator strip elastically bending in response to a proximal flow of air through the internal passageway.

7. The device of claim 2 further including:

an adapter for coupling the tubular wand in fluid communication with a standard vacuum line.

8. The device of claim 7 further including:

a coupling means, mounted to the adapter and to the proximal end of the tubular wand, for releasably interlocking the adapter and the wand.

9. The device of claim 7 further including:

a valve means mounted within the adapter, for controlling the flow of air through the adapter.

10. An exhaust system for removing the airborne elements generated as a product of a surgical procedure, including:

an elongate hand-held wand having a proximal opening at its proximal end and a distal opening at its distal end, and defining an internal passageway for accommodating a flow of air from the distal opening to the proximal opening;

a partition means disposed inside of the wand and dividing the internal passageway into an upstream chamber in direct fluid communication with the distal opening, and a downstream chamber in direct fluid communication with the proximal opening; said partition means including a filtering means for allowing the flow of air therethrough while collecting airborne elements within the flow of air, to prevent passage of the airborne elements into the downstream chamber;

a means for mounting the partition means to the housing;

a length of vacuum tubing having a proximal end and a distal end adapted for removable coupling to the proximal end of the wand to establish fluid communication with the proximal opening; and a vacuum source in fluid communication with the proximal end of the vacuum tubing, for drawing air through the vacuum tubing in the proximal direction, thus to generate an air flow through the internal passageway of the wand.

11. The system of claim 10 further including:

an adapter for coupling the distal end of the vacuum tubing with the proximal end of the wand, said adapter including a proximal portion suited for frictional engagement with the vacuum tubing, and a coupling means at its distal end for releasably interlocking with a complementary coupling means near the proximal opening of the wand.

12. The system of claim 11 further including:

a valve means mounted in the adapter, for controlling the flow of air through the adapter.

13. The system of claim 10 further including:

an indicator means for visually indicating the flow of air through the internal passageway of the wand.

14. The system of claim 13 wherein:

the wand is tubular and transparent, and the indicator means are mounted inside of the wand near the distal opening.

* * * * *